United States Patent [19]
Werner et al.

[11] Patent Number: 5,285,762
[45] Date of Patent: Feb. 15, 1994

[54] METHOD AND ARRANGEMENT FOR MONITORING THE OPERABILITY OF A PROBE HEATING DEVICE

[75] Inventors: Peter Werner, Wiernsheim-Iptingen; Hermann Hemminger, Markgroeningen; Hubert Schweiggart, Stuttgart; Andreas Werner, Reichenbach, all of Fed. Rep. of Germany

[73] Assignee: Robert Bosch GmbH, Stuttgart

[21] Appl. No.: 862,567

[22] PCT Filed: Nov. 10, 1990

[86] PCT No.: PCT/DE90/00858
§ 371 Date: Jun. 22, 1992
§ 102(e) Date: Jun. 22, 1992

[87] PCT Pub. No.: WO91/09219
PCT Pub. Date: Jun. 27, 1991

[30] Foreign Application Priority Data

Dec. 20, 1989 [DE] Fed. Rep. of Germany .... 3941995.9

[51] Int. Cl.$^5$ .............................................. F02D 41/14
[52] U.S. Cl. ...................... 123/60; 123/697; 204/401
[58] Field of Search ............... 123/479, 688, 690, 697; 204/401, 425

[56] References Cited

U.S. PATENT DOCUMENTS

| | | | |
|---|---|---|---|
| 4,419,190 | 12/1983 | Dietz et al. ......................... | 204/425 |
| 4,724,815 | 2/1988 | Mieno et al. ........................ | 123/690 |
| 4,958,611 | 9/1990 | Uchinami et al. ............... | 123/697 X |
| 5,090,387 | 2/1992 | Mayer et al. ........................ | 123/479 |

FOREIGN PATENT DOCUMENTS 005613 11/1979 European Pat. Off. .
0068323 1/1983 European Pat. Off. .
60-93140 5/1985 Japan .

OTHER PUBLICATIONS

"Das Opel-Diagnose-Konzept aus der Sicht des Entwicklers-Status und zukünftige Anforderungen" by K. Gebhardt et al in Elektronik in Kraftfahrzeug, VDI Berichte 687, Sep. 1988, pp. 349 to 359.
"Strategy for a Fail-Safe Electronic Diesel Control System for Passenger Cars", by G. Stump et al, SAE Technical Paper Series 830527, Mar. 1983, pp. 81 and 82.

Primary Examiner—Tony M. Argenbright
Attorney, Agent, or Firm—Walter Ottesen

[57] ABSTRACT

A system for monitoring the operability of a probe heating device is introduced which comprises a probe heater, an arrangement which supplies the probe heater with the necessary electrical energy and the corresponding supply leads. The essence of the invention is that the heating current for a probe heater causes a measuring voltage on a measuring resistor connected in series with the probe heater. The measuring voltage is compared to a further voltage which is emitted by a reference element. The reference element is at a similar temperature as the measuring resistor or receives a measuring signal which corresponds to the temperature of the measuring resistor and emits a voltage which has a similar temperature response as the measuring voltage. By means of this comparison of both voltages, it is possible to conclude as to the current flowing through the heater and therefore as to the operability of the probe heating device without switching too high a resistor in series with the probe heater.

16 Claims, 4 Drawing Sheets

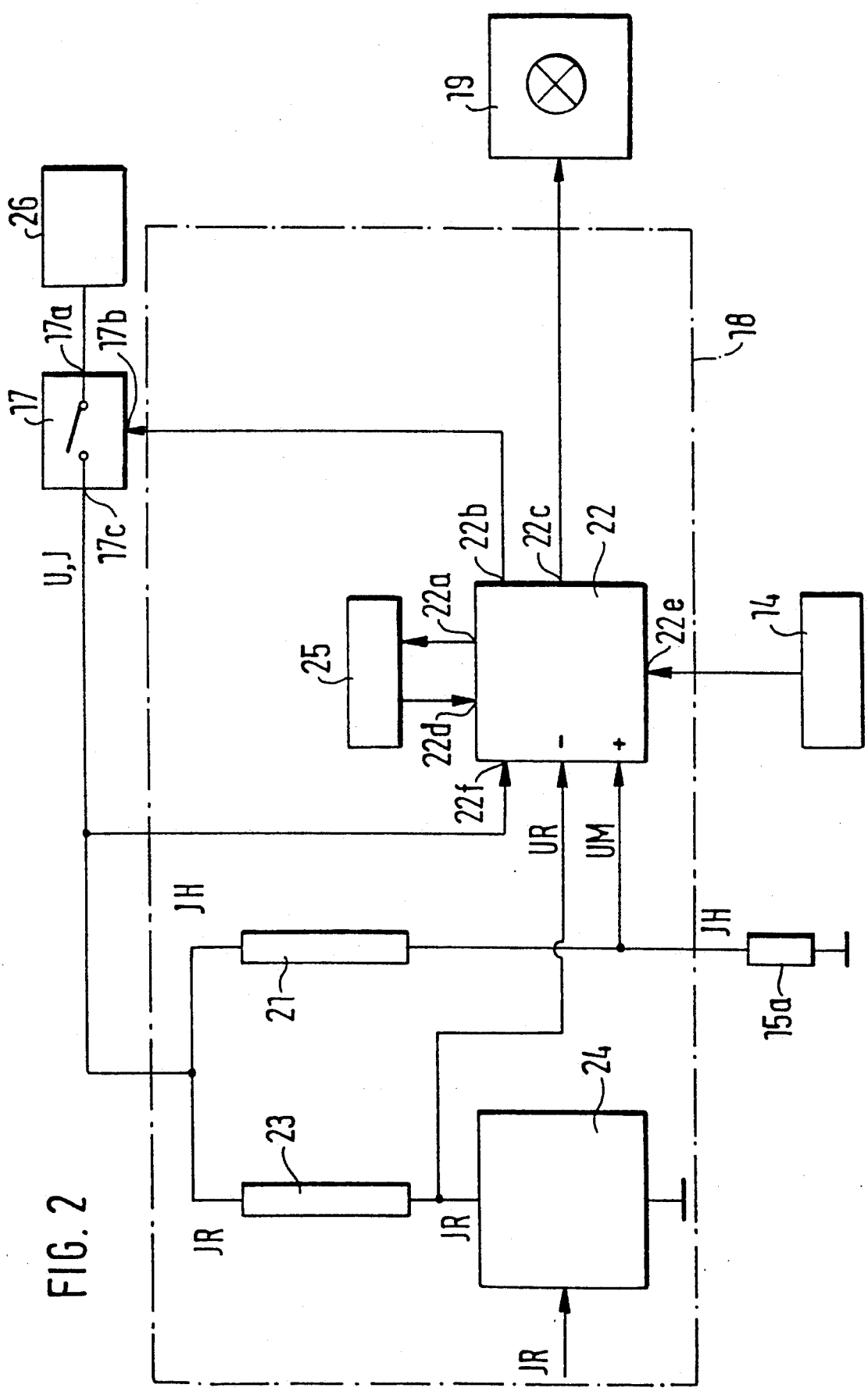

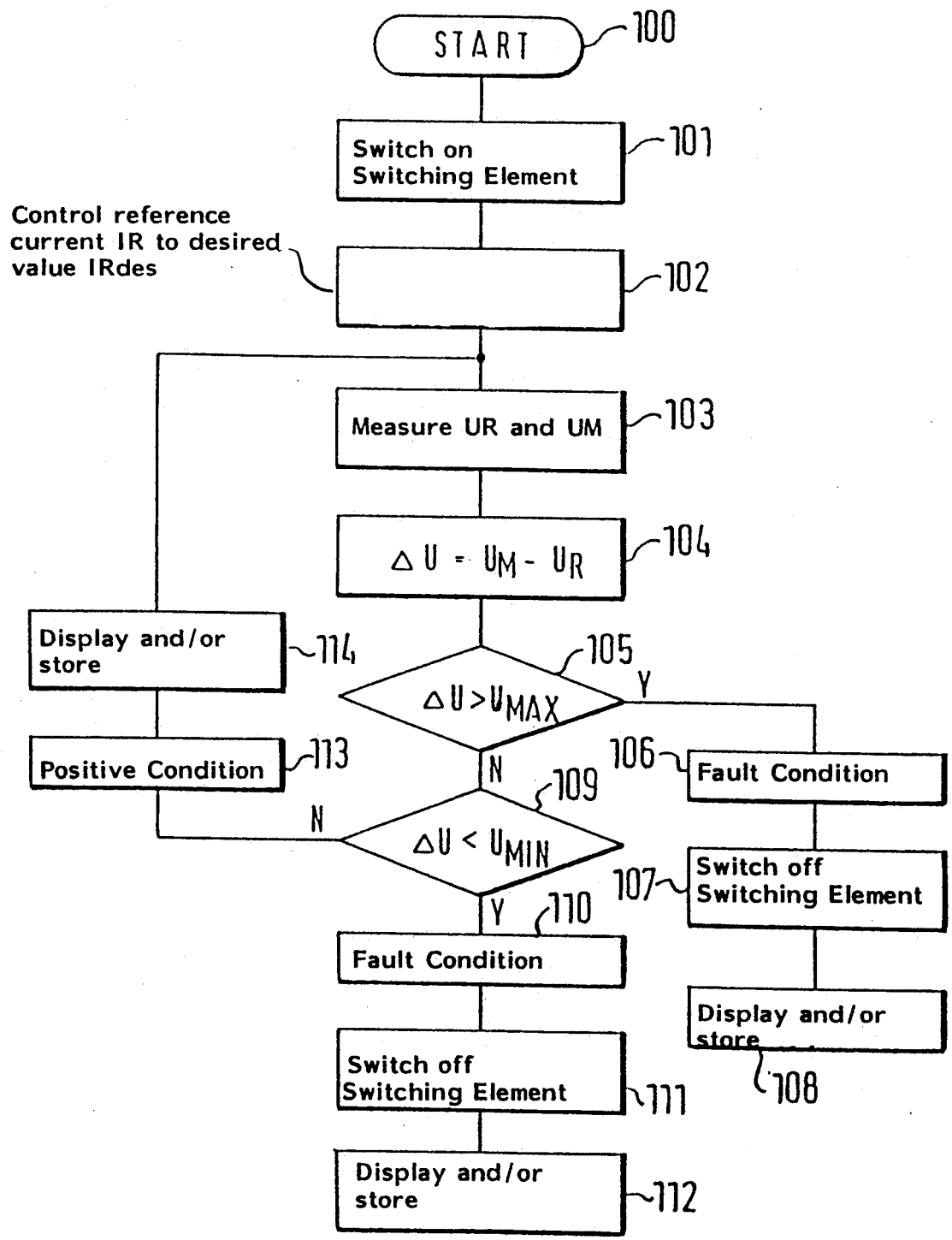

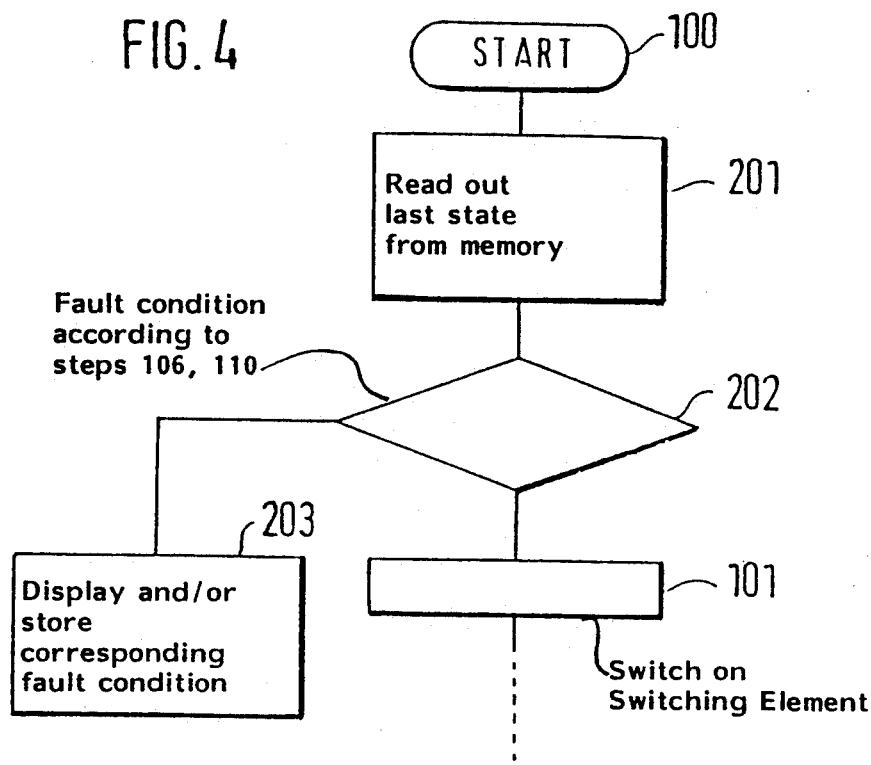
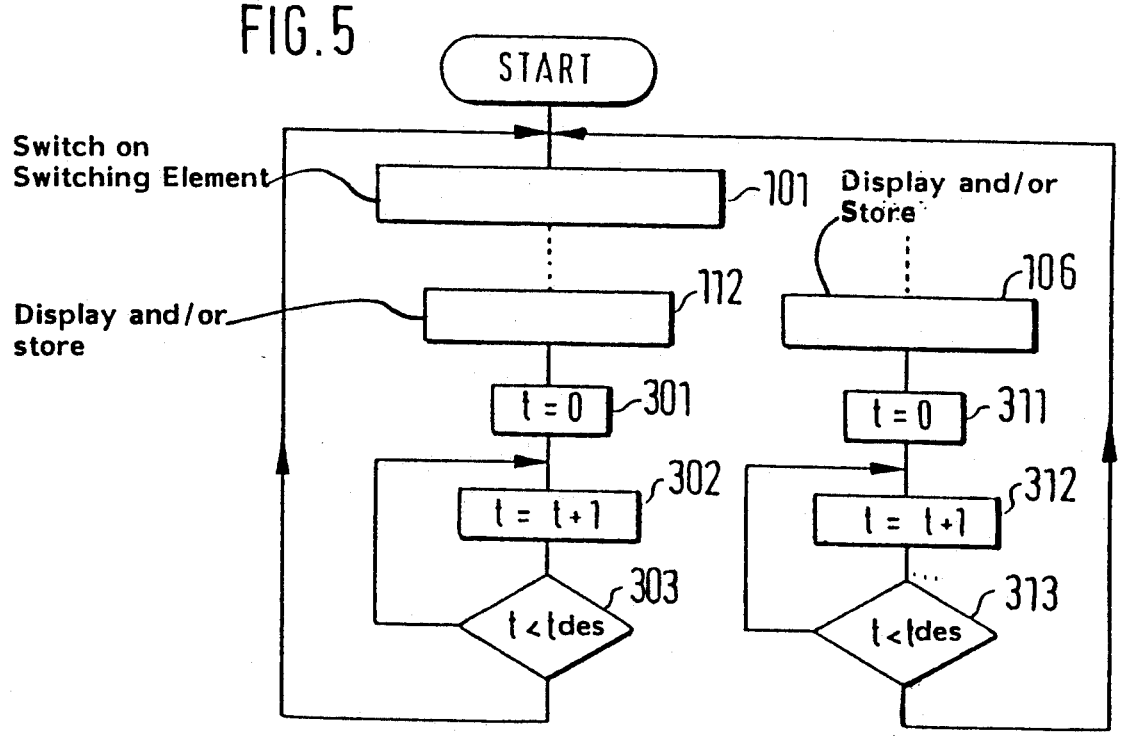

METHOD AND ARRANGEMENT FOR MONITORING THE OPERABILITY OF A PROBE HEATING DEVICE

FIELD OF THE INVENTION

The method of the invention and the arrangement for carrying out the method relate to the monitoring of the operability of a probe heating device which includes at least one probe heater, at least one device which supplies the probe heater with electrical energy and the supply leads corresponding thereto.

BACKGROUND OF THE INVENTION

It is known to provide control arrangements for maintaining a specific air/fuel ratio of the air/fuel mixture supplied to an internal combustion engine. The control arrangements receive their control variables from an oxygen measuring probe mounted in the exhaust gas system of the internal combustion engine. In general, this control is superposed on a known mixture control arrangement which coarsely precontrols the composition of the air/fuel mixture. The precondition for a trouble-free operation of such a control arrangement is that the oxygen measuring probe operates without trouble. In known oxygen measuring probes, the operational readiness is assured only after a specific operating temperature. For this reason, and for probes which are heated only by the exhaust gas of the internal combustion engine, a mixture control must be provided for the cold start and the warm running of the engine. The mixture open-loop control is replaced by a mixture closed-loop control only after reaching the probe temperature which increases with the operating temperature of the internal combustion engine.

A method and an arrangement for temperature control of an exhaust gas probe is known from U.S. Pat. No. 4,419,190. This method and arrangement convert the temperature-dependent electrical resistance of the oxygen measuring probe into a temperature signal and, thereafter, drive a heating device for heating the exhaust gas probe. In this way, the operating temperature of the exhaust gas probe can be maintained constant in a simple manner and without additional sensors and measuring leads.

The operability of the probe heater is a precondition so that the exhaust gas sensor reaches its operating temperature as rapidly as possibly and thereafter is also maintained at a pregiven temperature.

Furthermore, the exhaust gas probe can be destroyed if a current flows therethrough having a value greater than that of a permissible current.

A system for monitoring the operability of a heater for an exhaust gas probe is already introduced in U.S. Pat. No. 5,090,387. Here, the operational readiness of the exhaust gas probe is monitored and a conclusion is drawn as to its operability in dependence upon the time-dependent response between switch-on of the probe heater and the detection of the operational readiness.

However, if a current flows through the exhaust gas probe having a value above a permitted range, this is not immediately detected by the system of the mentioned application but only when there is a possible complete malfunction of the exhaust gas probe.

SUMMARY OF THE INVENTION

The method of the invention and the arrangement required for carrying out the method afford the advantage that they monitor the current flowing through the probe heater in such a manner that a current through the probe heater which is too high as well as a current through the probe heater which is too low is detected.

Only when the probe heater operates properly, can it be ascertained that the exhaust gas probe, on the one hand, rapidly reaches its operating temperature range and also maintains this range during operation and, on the other hand, is not overheated by a current which is too high.

In the first case, the probe heats up in dependence upon the exhaust gas temperature and the exhaust gas composition significantly slower and can, for example in overrun operation, cool off again. This leads to the situation that the ratio of the air/fuel mixture supplied to the internal combustion engine is determined more often by open-loop operation, by means of which the desired air/fuel ratio cannot be maintained with such precision, than by closed-loop operation. This leads to exhaust gas emissions having a higher portion of toxic components.

In the second case, that is when the probe overheats, the probe can be affected in its operating capability and its measuring performance whereby its output signal can be falsified. It is also possible that the probe becomes destroyed whereby an exchange thereof is required with a corresponding cost.

However, if the determination is made by the method according to the invention that the probe current does not lie within pregiven limits, then this result can be made known to the driver by means of a display device, stored in a memory and/or an arrangement which supplies the probe heater with electrical energy can be separated therefrom. In this way, the driver can take appropriate measures for restoring the operational readiness of the probe heater and a possible destruction of the probe by overheating is avoided.

In this way, requirements of the California Environmental Authority CARB are satisfied which requires that the malfunction of parts relevant to exhaust gas (these include the probe heater) is indicated and displayed.

BRIEF DESCRIPTION OF THE DRAWINGS

Embodiments are shown in the drawing and explained in greater detail in the following description.

FIG. 2 shows the arrangement for monitoring the current through the probe heater, that is, the flowing current;

FIGS. 3 to 5 are flowcharts of various versions of the monitoring method.

DESCRIPTION OF THE PREFERRED EMBODIMENTS OF THE INVENTION

Figure 1:
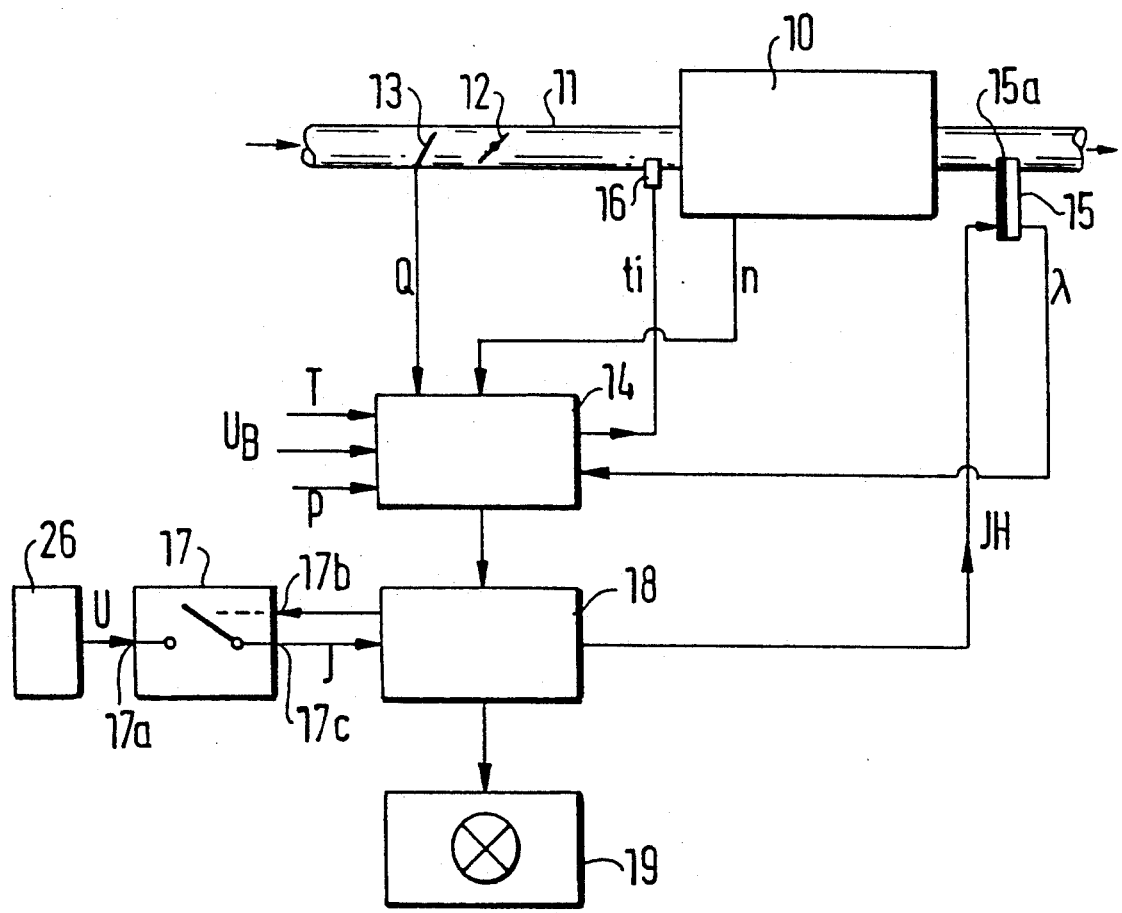
FIG. 1 shows a possible realization form of electronic and electrical closed-loop and open-loop control elements as well as actuator members for the operation of an internal combustion engine with this figure being shown as a simplified schematic in the form of a block circuit diagram.

The basic idea of the present invention is that the voltage (measuring voltage UM), which drops across a resistor (measuring resistor) when a heater current IH flows, is detected and evaluated. The resistor is connected in series with the probe heater.

Since very large currents flow through the probe heater and therefore also through the measuring resistor during the heat-up phase, the voltage dropping across the measuring resistor causes a thermal energy of:

$$P = UM \cdot IH \text{ or } P = RM \cdot IH^2.$$

That is, the greater the voltage UM available for measurement or the greater the resistor value RM of the measuring resistor are, the higher the power P and the lower the voltage available for the probe heater become since the measuring resistor and the internal resistance of the probe heater define a voltage divider.

If the measuring resistor has a low resistance value RM, the voltage UM dropping thereacross is also less and therefore also the power P dropping thereacross. On the other hand, for low measuring voltages UM, such as caused by tolerances of the measuring devices used, measuring errors also are greater.

An additional voltage UR (reference voltage) is emitted by a reference element which is maintained at a similar temperature as the measuring resistor or this reference element receives a corresponding temperature signal and its voltage UR has a similar temperature response as the measuring voltage UM. By comparing the measuring voltage UM to the further voltage UR, a reliable statement is possible as to the current flowing through the probe heater even for very low measuring voltages UM. In this way, a diagnosis of the entire heating device is possible. The heating device includes at least the probe heater, a device which supplies the probe heater with the necessary electrical energy and the supply leads corresponding thereto.

The reference element can, for example, be a second resistor (reference resistor) on which a pregiven current is impressed with the second resistor having a temperature response corresponding to that of the measuring resistor and which is maintained at a like temperature.

This is obtained preferably in that the measuring resistor and the reference resistor are configured as film resistors.

Film resistors (thin-film and thick-film resistors) are understood to be those which are manufactured by structuring an electrically conductive material (such as metal). This electrically conductive material can be applied to a substrate by vaporization, by sputtering, by a galvanic or other physical/chemical process known to the expert in this area.

The measuring resistor and the reference resistor are disposed on a common substrate and are formed by the same electrically-conductive material of the same thickness. For this reason, it is ensured that they are held approximately at the same temperature and have similar temperature responses.

The reference element can, however, also be configured differently. An electronic stage is plausible which receives a signal from a temperature sensor as to the temperature of the measuring resistor and emits a voltage in response thereto which is approximately the same as the temperature response of the measuring resistor.

Before the invention is considered in greater detail, it is emphasized that the block circuit diagram shown in FIG. 1 and showing the invention in the context of discrete circuit components does not limit the invention; instead, it serves especially to make clear the functional basic operations of the invention and to point out special functional sequences in a possible form of realization. It is understood that the individual components and blocks can be assembled in analog, digital or hybrid technology. Furthermore, it is also possible that the components and blocks include corresponding areas of program-controlled digital systems such as microcomputers, microprocessors, digital or analog logic circuits and the like. The following descriptions are therefore only to be seen as preferred embodiment with reference to the functional overall and time sequence with the suggestions as to the particular circuit blocks being provided for an improved understanding.

In FIG. 1, an internal combustion engine 10 is shown having an intake area 11 in which, among others, a throttle flap 12 is disposed which determines the quantity of air supplied to the engine 10 because of its deflection from its rest position. An air flow sensor 13, which measures this air quantity, supplies an output signal Q to an electronic control unit 14 which is usually a microcomputer having a microprocessor, a memory corresponding thereto as well as a current supply and receives additional data as to operating state such as: the rotational speed (n) of the engine, the air/fuel ratio supplied to the engine, which is determined by an output signal of an exhaust gas probe which is especially here a lambda probe 15. The lambda probe 15 is mounted in the exhaust gas channel of the engine and provides actual-value data as to the particular operating state of the engine, more precisely as to the oxygen content in the exhaust gas.

From this data and a plurality of further supplied data such as temperature (T), air pressure (p) and the like ($U_{BAT}, \ldots$), the electronic control unit 14 produces an output signal computed with high accuracy, in a fuel injection device for example an injection control command ti for driving injection valves illustrated with 16 in the intake area.

The exhaust gas probe 15 is equipped with a probe heater 15a which is driven by a circuit element 17 and is connected to a voltage source 26 which supplies the exhaust gas probe with electrical energy. The voltage source is usually so configured that it is continuously switched on during operation of the engine. The switching element 17 includes a supply input 17a, a control input 17b as well as an output 17c. The contact of the switching element 17 is closed when a control signal is applied to the input 17b so that a voltage U occurs at its output 17c when contact resistances are negligible. The voltage U is supplied by a voltage source 26 and is present at the supply input 17a.

A diagnostic block 18 is provided for carrying out the diagnostic process and is shown separately in FIG. 1 but can also be part of a central microcomputer. This diagnostic block receives signals of the electronic control unit 14 and emits control signals to the switching element 17 which is connected to the output of a voltage supply 26. The diagnostic block 18 further supplies results of the diagnosis to a display device 19 and includes a memory in which values of the received signals and of the results determined by the diagnostic block can be stored.

If the display device 19 is driven by the diagnostic block 18 then this display device illuminates in accordance with the result of the diagnosis for example with indicator lamps. It is understood that this display is basically in any desired form and can be realized also as an alpha display and can also display intermediate values of the diagnosis. Furthermore, it is also possible that the driver is informed by acoustic or other signals.

At the start of the engine 10, the diagnostic block 18 receives a command from the electronic control unit 14 to supply a pulse to the switching element 17 so that the probe heater 15a is supplied with the necessary electrical energy.

The current I, which flows from the voltage source 26 through the diagnostic unit 18, is composed of a heater current IH, which flows through the probe heater, and of further currents which are discussed further below. The value of the heater current IH is detected by the diagnostic block 18 and compared to pregiven minimum and maximum values.

If the heater current IH lies outside of the tolerance range, that is below the minimum or above the maximum value, this is detected by the diagnostic block 18 and the block 18 emits a signal to the display device 19 whereby the driver is signalled as to a corresponding defect condition. Furthermore, a signal can be emitted to the switching element 17 so that the voltage source 26 is separated from the feed system of the probe heater.

FIG. 2 shows a preferred embodiment of the diagnostic block 18. The diagnostic block 18 contains a measuring resistor 21 which is connected outwardly with its one end to the switching element 17 and, with its other end, to a positive input of a comparator stage 22 which is part of the diagnostic block 18. A reference resistor 23 is likewise connected to the switching element 17 with its one end and, with its other end, to a constant current source 24 as well as to the negative input of the comparator stage 22.

The current IR impressed by the constant current source is controlled to a desired value IRdes which can be supplied from outside. The comparator stage 22 has three outputs with the first output 22a being connected to a memory 25, the second output 22b being connected to the control input 17b of the switching element 17 and the third output being connected to the display device 19. In addition, the following are provided: an input 22d via which the content of the memory 25 can be read in, an input 22e via which signals of the electronic control unit 14 reach the comparator stage 22, and an input 22f on which the voltage U is present which is also applied to the common connection of the resistors (21, 23).

The sequence of the method of the invention and the function of the arrangement of the invention are explained with respect to FIG. 3. When the engine is started (step 100), a start signal by the electronic control unit 14 is supplied to the comparator stage 22. Thereafter, the switching element 17 is connected by a control signal of the comparator stage 22 so that the voltage U of the voltage source 25 is applied to the common terminal of the measuring resistor 21 and the reference resistor 23 when contact resistances can be neglected. The measuring resistor 21 is connected in series with the probe heater 15a. Essentially the heater current IH flows through the measuring resistor 21 since the current flowing into the positive input of the comparator stage 22 can be neglected.

Since the reference resistor is connected with its second terminal to the constant current source 24, after a certain transient time, the current IR determined by the constant current source flows through the reference resistor and corresponds essentially to the desired value IRdes (step 102).

Thereafter, the voltage UM which drops across the measuring resistor 21 when the heating current IH flows therethrough, is measured by the comparator stage 22 as is the voltage UR which drops across the reference resistor 23 when the reference current IR flows therethrough (step 103) and a difference $\Delta U = UM - UR$ is formed by the comparator stage 22 (step 104).

At this point, it should again be noted that the reference voltage can also be emitted by an electronic stage which receives a signal which is a measure for the temperature of the measuring resistor and then emits a voltage which has the same temperature response as the voltage UM dropping across the measuring resistor.

In step 105, the difference $\Delta U$ is compared to the highest permissible maximum value MAX. If $\Delta U$ is greater than MAX, then the method according to the invention continues with step 106 where a fault condition is detected. This fault condition permits a conclusion of a heater current IH which is too great, which, for example, can be caused by a short circuit in the probe heater 15a or in the lead system leading to the probe heater. It is however also possible that the voltage U at the voltage source 26 is greater than a highest permissible value whereby a current which is too large can flow through the probe heater.

Thereafter, step 107 follows in which a signal of the comparator stage 22 is emitted to the switching element 17 whereby the switching element separates the voltage source 26 from the diagnostic block 18 and therefore also from the probe heater 15a. In step 108, signals are emitted by the comparator stage 22 to the display device 19 and/or to the memory 25 whereby a fault condition can be signalled to the driver or stored in the memory 25.

However, if step 105 results in that $\Delta U$ is not greater than MAX, then a comparison of $\Delta U$ to a minimal permissible value MIN takes place in step 109. If $\Delta U$ is less than MIN, then a fault condition is present of the kind that the heater current IH is too small which permits the following conclusions: a line interruption to the probe heater 15a or in the probe heater 15a; high contact resistances, for example, in the connections not shown; or, a voltage U of the voltage source 26 which is too low (step 110).

The switching element 17 is switched off (step 111) by a signal of the comparator stage 22 whereby the connection of the voltage source 25 to the diagnostic block 18 and therefore also to the probe heater 15a is interrupted.

The result of this fault condition can also be signalled to the driver or stored in memory 25 (step 112).

If the inquiry in step 109 yields that $\Delta U$ is greater than or equal to MIN, then $\Delta U$ and therefore also the heater current IH lie in the pregiven tolerance range (MIN, MAX) so that a good condition is present (step 113). This too can be displayed to the driver or stored in memory 25 (step 114).

In order to not immediately reach the storage capacity of the memory 25, not all positive conditions must be permanently stored in step 114; instead, only the last one or last ones.

According to a variation of the mentioned embodiment, intermediate steps are inserted between the steps 100 and 101 (FIG. 4) in order to inquire as to the last condition(s) from the steps 106, 110 or 113 in advance of switching off the engine and to evaluate the condition(s) before switching on the switching element 17 (step 101).

The variation shown in FIG. 4 likewise starts with step 100 with the start of the engine. In step 201, the last condition (fault condition/positive condition) is read out of memory 25 and an inquiry is made in step 202 as to whether there is a fault condition according to step 106 or according to step 110. If so, then a corresponding display and/or (repeated) storage of the fault condition present takes place. If no fault condition is determined in step 202, then the method is continued starting with step 101.

A second embodiment of the method of the invention comprises that after display/storage of a fault condition according to steps 108 or 112, the switching element 17 is again switched in after a specific time and that the method continues according to the first version already described.

For this purpose, a time element is integrated into the comparator stage 22 which again starts the method with step 101 after a pregiven time has elapsed. The supplements of the flowchart are shown in FIG. 5.

A step 301 follows step 112 in which a time counter is set to zero. In step 302, the time counter is increased (incremented) by one and in step 303, an inquiry is made as to whether a pregiven time tdes has already passed. If no, the method again reaches step 302. This loop is run through until t=tdes. Then the method of the invention goes to step 101 whereby the sequence already described with respect to FIG. 3 is started again.

The same applies for the sequence starting with step 106. The steps 311 to 313 mentioned here correspond to the steps 301 to 303.

The purpose of this embodiment is that, for example, the condition can be present because of overheating that the heating current IH lies only temporarily outside of the pregiven limits (MIN, MAX).

A temporary switch-off of the heating current IH is therefore necessary especially for overheating.

A system for monitoring the operability of a probe heater device is introduced which includes: a probe heater, an arrangement which supplies the probe heater with the necessary electrical energy and the necessary supply leads. The essence of the invention is that the heater current for a probe heater causes a measuring voltage on a measuring resistor connected in series with the probe heater with the measuring voltage being compared to a further voltage which is supplied by a reference element. The reference element is at a similar temperature as the measuring resistor or receives a measuring signal which corresponds to the temperature of the measuring resistor and emits a voltage which has a temperature response similar to that of the measuring voltage. By means of the comparison of the two voltages it is possible to draw a conclusion as to the current flowing through the probe heater and therefore as to the operability of the probe heater device without having to connect a resistor, which is too high, to the probe heater.

We claim:

1. A method for monitoring the operability of a probe heating device, which includes at least one probe heater, an arrangement which supplies the probe heater with the necessary electrical energy and the supply leads corresponding thereto, the probe heating device being for an exhaust gas probe, which operates for controlling the air/fuel ratio of an air/fuel mixture supplied to an internal combustion engine, the method comprising the steps of:
    detecting a heating current (IH) flowing through the heating device by means of a voltage (UM) dropping across a measuring resistor;
    comparing the voltage (UM) to a voltage provided by a reference element, the reference element having a signal response the same as the measuring resistor; and,
    when the comparison results in a plausibility interval (UMIN, UMAX) is exceeded, drawing a conclusion as to a corresponding fault condition of the probe heating device and emitting a corresponding fault signal.

2. The method of claim 1, comprising the further steps of configuring the reference element as a reference resistor on which a constant current is impressed, and configuring the reference resistor and the measuring resistor as film resistors which are both disposed on a common substrate.

3. The method of claim 1, comprising the further step of determining a positive condition when the value of the heating current (IH) lies within the pregiven values and then emitting a corresponding signal, and then carrying out at least one of the following steps: transmitting signals with reference to the positive condition or of a possible fault condition to the operator; and, storing said signals with respect to the positive condition or of a fault condition in a memory.

4. The method of claim 1, comprising the further step of separating the probe heater from the arrangement which supplies the probe heater with the necessary electrical energy by means of the fault signal when a fault condition is present.

5. The method of claim 1, comprising the further steps of reading out first values from the memory after the start of the internal combustion engine, which first values permit a conclusion as to a positive condition or a fault condition of the heating device during the previous operating phase, and then, in dependence upon the read out values, connecting the exhaust gas probe to the arrangements which supply the probe with electrical energy.

6. The method of claim 1, comprising the further step of separating the probe heater only for a pregiven time from the arrangement which supplies the probe heater with electrical energy upon the occurrence of a fault condition.

7. The method of claim 1, comprising the further steps of:
    maintaining said reference element at a temperature similar to the temperature of said measuring resistor with said reference element providing a voltage (UR) exhibiting a temperature response similar to said voltage (UM);
    causing said measuring resistor to be connected in series with said probe heating device and permitting said heating current (IH) to produce a voltage (UM) on said measuring resistor; and,
    detecting said heating current (IH) by comparing said voltage (UM) to said voltage (UR).

8. The method of claim 1, comprising the further steps of:
    providing said reference element as an electronic device having an input and an output and said electronic device being adapted to simulate the temperature response of said measuring resistor;
    applying a signal to an input of said electronic device corresponding to the temperature of said measuring resistor thereby causing said electronic device to supply a voltage (UR) at said output thereof exhibiting a temperature response similar to said voltage (UM):
    causing said measuring resistor to be connected in series with said probe heating device and permitting said heating current (IH) to produce a voltage (UM) on said measuring resistor; and, detecting said heating current (IH) by comparing said voltage (UM) to said voltage (UR).

9. An arrangement for monitoring the operability of a probe heating device, which includes a probe heater, an arrangement which supplies the probe heater with the necessary electrical energy and the supply leads corresponding thereto, the probe heating device being for an exhaust gas probe, which serves to control the air/fuel ratio of an air/fuel mixture supplied to an internal combustion engine, the arrangement comprising:
a diagnostic block which includes:
a measuring resistor connected to the probe heater;
a reference element having a signal response the same as said measuring resistor and providing a voltage (UR);
means for supplying a heating current (IH) to flow through said measuring resistor and said probe heater to cause a voltage (UM) to drop across said measuring resistor;
means for comparing the voltage (UM) to said voltage (UR); and,
means for drawing a conclusion as to a corresponding fault condition of the probe heating device and emitting a corresponding fault signal when the comparison results in a plausibility interval (UMIN, UMAX) which is exceeded.

10. An arrangement for monitoring the operability of a probe heating device, which includes a probe heater, an arrangement which supplies the probe heater with the necessary electrical energy and the supply leads corresponding thereto, the probe heating device being for an exhaust gas probe, which serves to control the air/fuel ratio of an air/fuel mixture supplied to an internal combustion engine, the arrangement comprising: a diagnostic block which detects the heating current flowing through the heating device and then, when the value of this heating current drops below or exceeds pregiven values, concluding that a corresponding fault condition of the probe heating device is present and emitting a corresponding fault signal; and,
said diagnostic block including a measuring resistor connected in series with the probe heater across which a voltage (UM) drops with the presence of a heating current (IH); a reference element which is maintained at a similar temperature as the measuring resistor or to which a signal is supplied which corresponds to the temperature of the measuring resistor and which emits a reference voltage (UR) which has a similar temperature response as the voltage (UM); and, a comparator stage which measures the voltages (UM) and (UR), forms a difference value from (UM) and (UR) and then, when the difference value lies outside of pregiven values (MIN, MAX), concludes that a corresponding fault condition is present and emits a corresponding signal.

11. The arrangement of claim 10, wherein the reference element is configured as a reference resistor on which a constant current is impressed by a constant current source, and wherein the reference resistor and the measuring resistor are configured as film resistors which are both disposed on a common substrate.

12. The arrangement of claim 11, wherein the comparator stage concludes as to a positive condition and emits a corresponding signal when the difference value lies within the pregiven values (MIN, MAX) and wherein the signals with respect to the positive condition or a possible fault condition are optically or acoustically signalled to the operator by a display device.

13. The arrangement of claim 12, wherein a switching element is provided which separates the probe heater from the arrangement, which supplies the probe heater with the necessary electrical energy, when a fault signal occurs.

14. The arrangement of claim 13, wherein the comparator stage includes means which, after the internal combustion engine is started, reads out values from the memory which permit a conclusion as to positive conditions or fault conditions of the heating device during the previous operating phase, and wherein the comparator stage emits a signal for driving the switching element in dependence upon the read-out values.

15. The arrangement of claim 14, wherein the comparator stage has a time element by means of which, for the occurrence of a fault signal and switch-off of the switching element, the switching element is switched on again after a pregiven time.

16. The arrangement of claim 11, wherein the comparator stage concludes as to a positive condition and emits a corresponding signal when the difference value lies within the pregiven values (MIN, MAX) and wherein the signals with respect to the positive condition or a possible fault condition are stored in a memory.

* * * * *